(12) United States Patent
Couzens et al.

(10) Patent No.: US 12,090,289 B2
(45) Date of Patent: Sep. 17, 2024

(54) PORTABLE NEEDLE ASSEMBLY WITH ADJUSTABLE LENGTH NEEDLE

(71) Applicant: CZDX Solutions, LLC, Southern Pines, NC (US)

(72) Inventors: John M Couzens, Southern Pines, NC (US); David A. Lux, Southern Pines, NC (US)

(73) Assignee: CZDX Solutions, LLC, Southern Pines, NC (US)

( * ) Notice: Subject to any disclaimer, the term of this patent is extended or adjusted under 35 U.S.C. 154(b) by 132 days.

(21) Appl. No.: 17/474,706

(22) Filed: Sep. 14, 2021

(65) Prior Publication Data

US 2022/0080160 A1 Mar. 17, 2022

Related U.S. Application Data

(60) Provisional application No. 63/077,709, filed on Sep. 14, 2020.

(51) Int. Cl.
*A61M 25/06* (2006.01)
*A61M 25/00* (2006.01)

(52) U.S. Cl.
CPC .... *A61M 25/0631* (2013.01); *A61M 25/0097* (2013.01); *A61M 2210/101* (2013.01)

(58) Field of Classification Search
CPC ........ A61M 25/0631; A61M 2210/101; A61M 1/04; A61M 25/0606; A61M 25/0612; A61M 25/0097; A61B 17/3415
See application file for complete search history.

(56) References Cited

U.S. PATENT DOCUMENTS

2016/0256667 A1* 9/2016 Ribelin ........... A61M 25/09041

* cited by examiner

*Primary Examiner* — Theodore J Stigell
(74) *Attorney, Agent, or Firm* — Outlier Patent Attorneys, PLLC (57) ABSTRACT

A needle assembly for treating tension pneumothorax includes an elongated needle disposed within an elongated catheter, and a housing for containing the needle and catheter. The needle is coupled to the housing through a length adjustment mechanism so that the needle and the catheter are configured to be deployed out of the distal end of the housing to a pre-determined length. The length adjustment mechanism may include an axial path in the wall of the housing, grooves extending off of the axial path, and a protruding arm coupled to the needle. The protruding arm of the needle is configured to extend through the axial path of the housing and be grasped by a user to deploy the needle and catheter out of the distal end of the housing. When the needle is deployed to a desired length, the user may lock the needle and catheter in place by positioning the protruding arm in the corresponding groove extending off of the axial path.

6 Claims, 5 Drawing Sheets

PORTABLE NEEDLE ASSEMBLY WITH ADJUSTABLE LENGTH NEEDLE

CROSS-REFERENCE TO RELATED APPLICATIONS

This application claims the benefit of, and priority to, U.S. Provisional Patent Application No. 63/077,709, filed Sep. 14, 2020, titled "PORTABLE NEEDLE ASSEMBLY WITH ADJUSTABLE LENGTH NEEDLE." That application is incorporated by reference herein in its entirety.

BACKGROUND

Field of the Art

This invention generally relates to a needle assembly for performing needle decompression to treat tension pneumothorax. More specifically, the needle assembly has an adjustable length needle so that the amount, or length, of needle that is deployed can be customized to the size of the patient.

Discussion of the State of the Art

Tension Pneumothorax (TPT) is a life-threatening condition that needs an immediate and appropriate response in order to prevent death. A TPT is often caused by blunt or penetrating trauma that allows air (oftentimes in concert with a hemothorax, which is blood in the pleural space) to build up in the chest cavity due to the presence of a hole or tear in the lung. The potential space surrounding the lungs, inside the chest, is called the pleural cavity. During normal breathing the pleural space is a potential space. It is found between the visceral pleural covering the surface of the lung and the parietal pleura lining the inner surface of the chest wall. If air leaks into the pleural space from a hole or tear in the chest wall and/or the lung, pressure may rapidly build inside the chest and constrict the flow of blood within great blood vessels that supply the heart. This ultimately leads to a diminished return of blood to the heart so that heart pump function is increasingly compromised. The untreated TPT will eventually diminish cardiac output to a point where the patient will expire due to the heart's inability to pump oxygenated blood to the rest of the body.

TPT is the second leading cause of death on the battlefield behind hemorrhage from extremity wounds, and is an injury pattern that can be seen on a daily basis in civilian life. A patient with a TPT must have the air or blood that is accumulating in their pleural space evacuated in order to allow the lung to re-inflate fully and the heart to continue getting blood, or they will eventually succumb to their injuries or wounds. Due to the lethality and regularity of the TPT, it is a military requirement for each deploying warfighter to have a Needle Decompression Kit (NDK) in the rucksack. In addition, NDKs can also be found in almost every ambulance, firetruck, and in most emergency rooms across the country. The decompression of the chest in the presence of a TPT is absolutely necessary, but has a very high failure rate upon execution (as high as 65%) of the procedure in the pre-hospital environment. The reasons for the failure rate being so high are quite varied, but two crucial causes of failure are: 1) the use of an imprecise tool to accomplish a very precise procedure, and, 2) improper application of the NDK due to lack of, or poor, instruction. Most warfighters receive a very brief refresher class on how to decompress a patient's chest prior to stepping out of the door for a deployment.

The military issues a standard NDK, containing a 3.25 inch, 14 gauge angio-catheter, to all deployed warfighters and first responders. The existing NDK contains an extremely large, one size fits all, needle. The reason for such a large needle dates back to Operation Desert Storm when some very muscular warfighters could not have their chests decompressed with smaller length needles. The response was to create a NDK containing a 3.25 inch 14-gauge angio-catheter that could enter into the pleural space of even the most muscular or obese patients. The 3.25 inch, 14 gauge angio-catheter will work on all patients, however it is appropriate for a very small percentage of the patient population. As a result, the vast majority of the patient population are now exposed to significantly increased risk due to the immense size of the NDK. Some pre-hospital organizations/agencies encourage their providers to "hub the needle." Many warfighters and medical providers do not have the appropriate level of education, or training, to safely perform a proper needle decompression. The result of this longer needle and lack of training leads to increased trauma to already injured patients with needles puncturing the lungs, liver, spleen, subclavian artery, heart, or other vital organs or essential structures.

What is needed is a portable, sturdy NDK that can be used in the field to reliably treat patients of a variety of sizes.

SUMMARY

The inventive apparatus disclosed herein is a needle assembly comprising a needle disposed within a catheter, wherein the needle and catheter are contained in a housing. The needle is coupled to the housing through a length adjustment mechanism so that the needle and catheter can be deployed out of the distal end of the housing to a predetermined length. In one embodiment, the length adjustment mechanism includes an axial path in a wall of the housing, grooves extending perpendicularly off of the axial path, and a protruding arm coupled to the needle. The protruding arm extends out of the housing through the axial path and/or the grooves. A user can deploy the needle and catheter out of the distal end of the housing by grasping the protruding arm and guiding it proximally or distally along the axial path in the housing until the desired exposed needle length is achieved. The needle and catheter may then be locked into the desired axial position by rotating the needle relative to the housing and positioning the protruding arm in one of the grooves. The catheter may have a protruding tab attached to the catheter proximal end so that a user may grasp the protruding tab to hold the catheter in place while the needle and housing are being withdrawn.

In another embodiment, a method for treating tension pneumothorax includes assessing a size of a patient, selecting a desired exposed needle length based on the size of the patient, and deploying the needle disposed within the catheter to the desired needle length. In one embodiment, the needle and catheter are deployed out of the distal end of the housing by grasping the protruding arm that is coupled to the needle, moving the protruding arm proximally or distally along an axial path in the housing until the exposed length of the needle and catheter are the desired length, and rotating the needle and protruding arm relative to the housing to move the protruding arm from the axial path into a groove extending perpendicular to the axial path, thereby locking the needle and catheter into the desired axial position. After the desired exposed needle length is attained, the needle may be used to perform needle decompression to treat tension pneumothorax.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION

The inventor has conceived, and reduced to practice, an apparatus, a system, and a method for performing needle decompression on a patient experiencing tension pneumothorax by using a NDK having an adjustable-length needle. That is, the amount, or length, of the portion of the needle that is exposed, or deployed, out of a housing is adjustable. Various embodiments of the inventive apparatus, system, and method are disclosed herein, including numerous alternative arrangements. However, it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

Conceptual Architecture

Disclosed herein is a needle decompression device in which the length of the exposed portion of the needle is adjustable in order to accommodate patients of varying sizes. In this manner, a first responder is able to carry only one needle decompression kit to treat patients of a variety of sizes in a safe and effective manner. As such, the needle decompression kit in accordance with the present invention is ideal for use in a pre-hospital setting since it is portable, packable, and easy to use in stressful, chaotic emergency situations.

Figure 1:
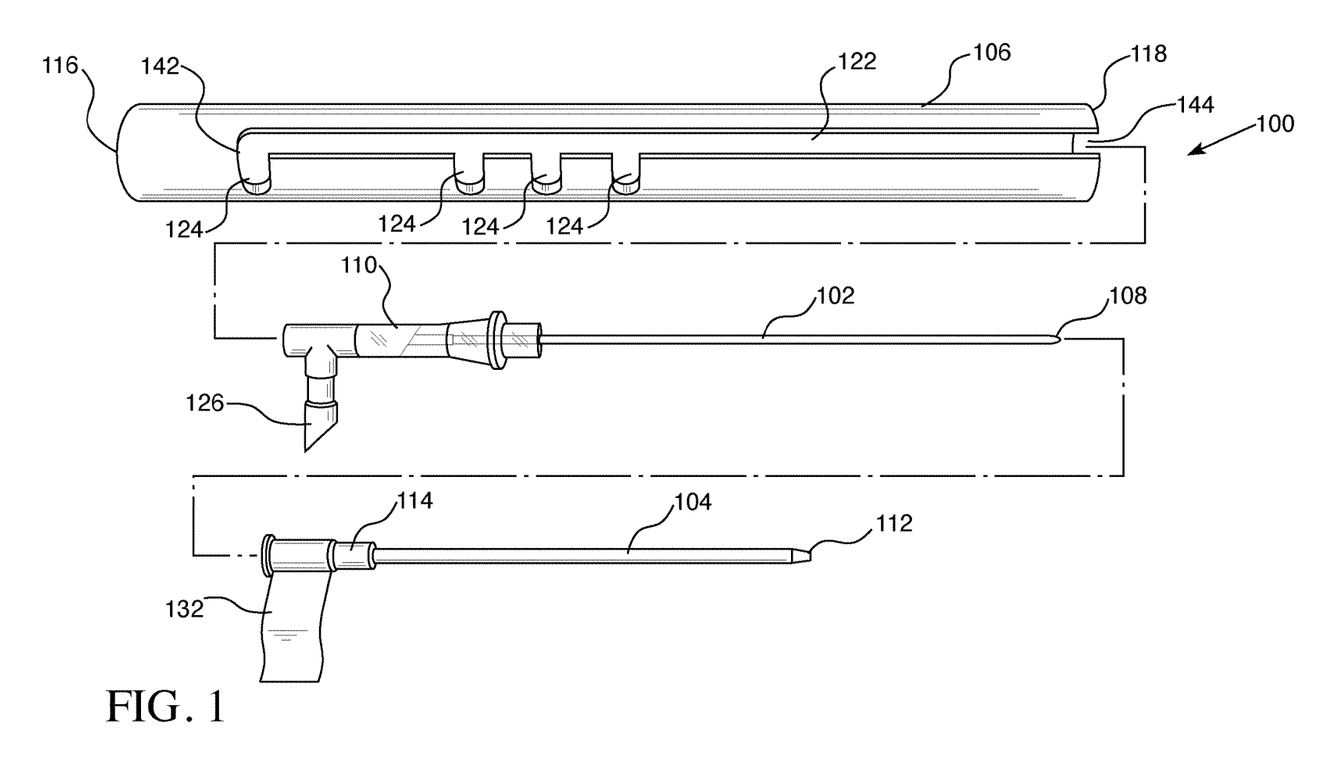
FIG. 1 is an exploded view of a needle assembly, in accordance with one embodiment of the invention.
Figure 2:
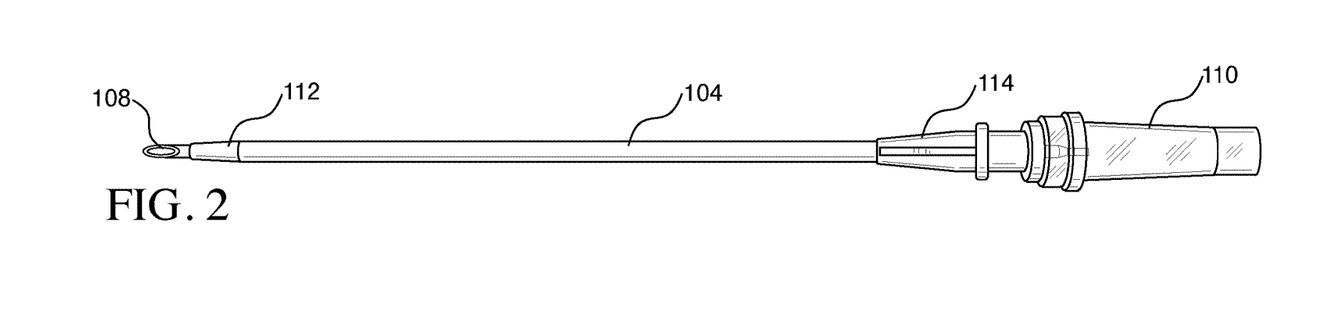
FIG. 2 is a side view of an assembled needle and catheter, in accordance with one embodiment of the invention.

A needle decompression kit 100 in accordance with the present invention is depicted in FIGS. 1-7. As shown in FIG. 1, the kit 100 includes a needle 102, a catheter 104, and a housing 106. The needle 102 has a sharpened distal end 108 and a needle hub 110 at the proximal end. The catheter 104 has a distal end 112, a catheter hub 114 at the proximal end, and a lumen extending between the catheter hub 114 and the distal end 112. The catheter lumen is configured to accommodate the needle 102 therein with the proximal needle hub 110 protruding from the proximal catheter hub 114 and the needle distal end 108 protruding from the catheter distal end 112. The needle 102 is longer than the catheter 104 so that the needle 102 extends the entire length of the catheter lumen when the needle 102 is positioned within the catheter lumen, as shown in FIG. 2. The needle 102 is inserted into the catheter 104, and is removed after the catheter distal tip 112 is positioned in the pleural space.

Figure 3:
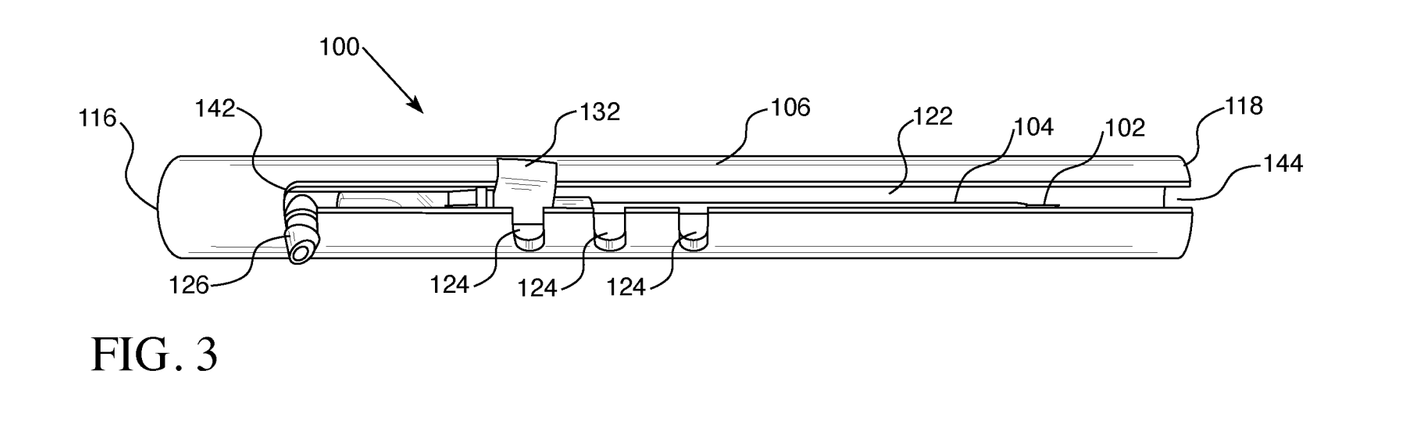
FIG. 3 is a side view of a needle decompression assembly, in accordance with one embodiment of the invention.

The housing 106 is sized and shaped to contain the entire length of the needle 102 and catheter 104, as shown in FIG. 3. As such, the housing 106 is longer than the needle 102 and the catheter 104, and has an inner diameter that is larger than the outer diameter of the catheter 104. FIG. 3 depicts the needle 102 positioned within the catheter 104, and the assembled needle 102 and catheter 104 disposed within the housing 106. The housing 106 has a closed proximal end 116 and an open distal end 118. The kit 100 may further include a removable cap (not shown) that can be attached to the distal end 118 of the housing 106 so that the needle 102 and catheter 104 are completely enclosed during storage and transportation of the kit 100. The cap is configured for quick and easy removal prior to using the kit 100. As such, the cap is intended to facilitate portability and packability of the kit 100. The housing 106 and cap are made of a rigid material, such as hard plastic or metal, so that the needle 102 and catheter 104 are protected from damage when they are positioned within the housing 106 with the cap attached to the housing 106.

In a conventional needle decompression kit, such as that made by North American Rescue, which is disclosed in U.S. Patent Application Publication No. 2017/0232164, hereby incorporated herein by reference, the needle and catheter are removed from the housing and then used to pierce through the patient's skin and chest wall until the distal end of the needle and catheter are inserted into the pleural space to treat tension pneumothorax. However, in a conventional needle decompression kit, where only a single needle length is available, the needle length may be too long to treat a smaller sized patient, and the excessive needle length may cause damage to the patient. Similarly, the needle length in a conventional needle decompression kit may be too short to treat a larger patient. The needle length may be insufficient to pierce through an excessively thick chest wall, rendering a conventional needle decompression kit ineffective for treating larger patients.

The needle decompression kit 100 in accordance with the present invention includes a needle length adjustment mechanism so that a medical provider can assess the patient, determine an appropriate needle length based on the size of the patient, and then deploy the needle 102 and catheter 104 out of the distal end 118 of the housing 106 to the desired needle length. The needle 102 and attached catheter 104 are axially moveable relative to the housing 106 so that the needle penetration depth can be adjusted based on the size of the patient. In this manner, the medical provider only needs to carry a single device that can be used to safely treat a patient of any size. For example, a longer exposed needle length is desirable if the patient is large, muscular, or obese, while a smaller exposed needle length is desirable if the patient is smaller, petite, or thin. A smaller patient has a chest wall that is much thinner than that of a larger patient. Using a standard length needle may be too small for larger patients and too large for smaller patients. A needle that can be selectively deployed to various exposed needle lengths allows for adjustable penetration depth to accommodate patients of different sizes.

Figure 4:
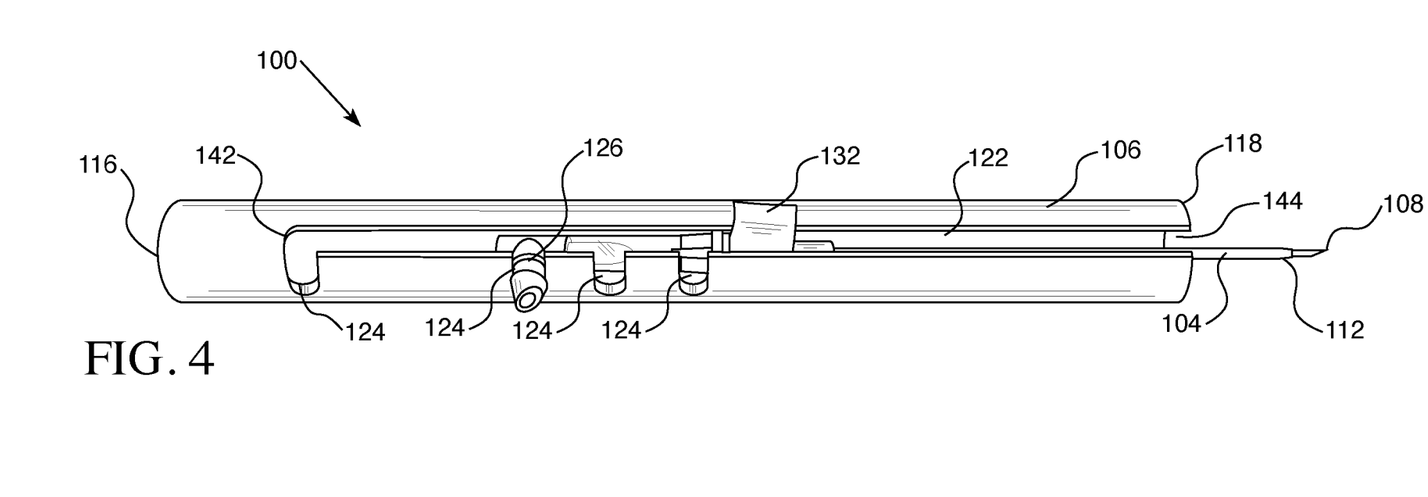
FIG. 4 is a side view of the needle decompression assembly deployed to a first length setting, in accordance with one embodiment of the invention.
Figure 5:
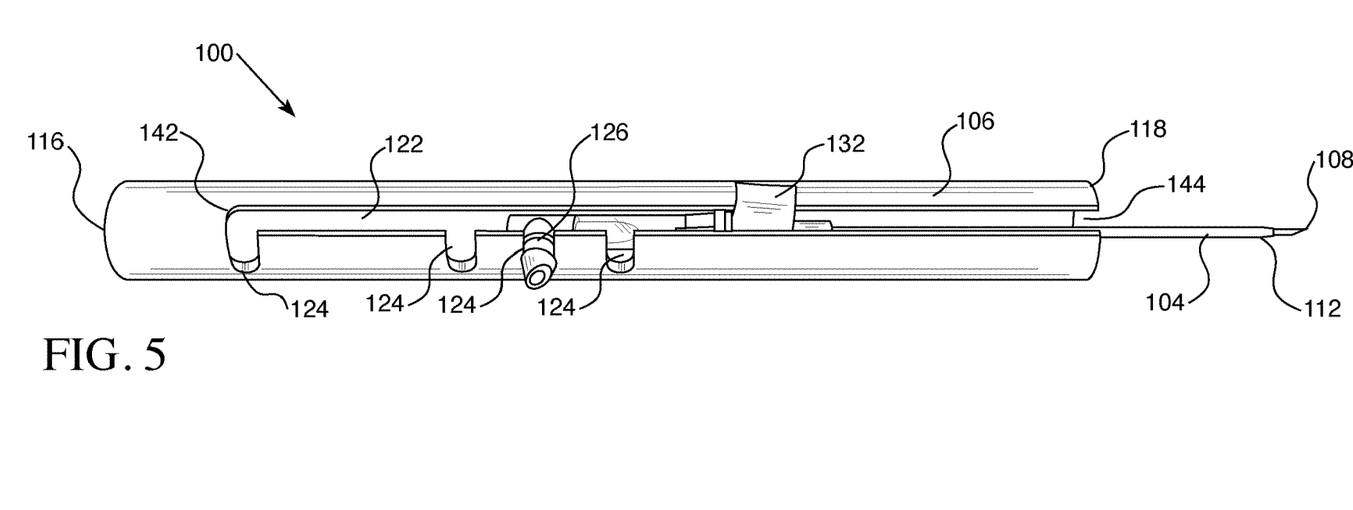
FIG. 5 is a side view of the needle decompression assembly deployed to a second length setting, in accordance with one embodiment of the invention.
Figure 7:
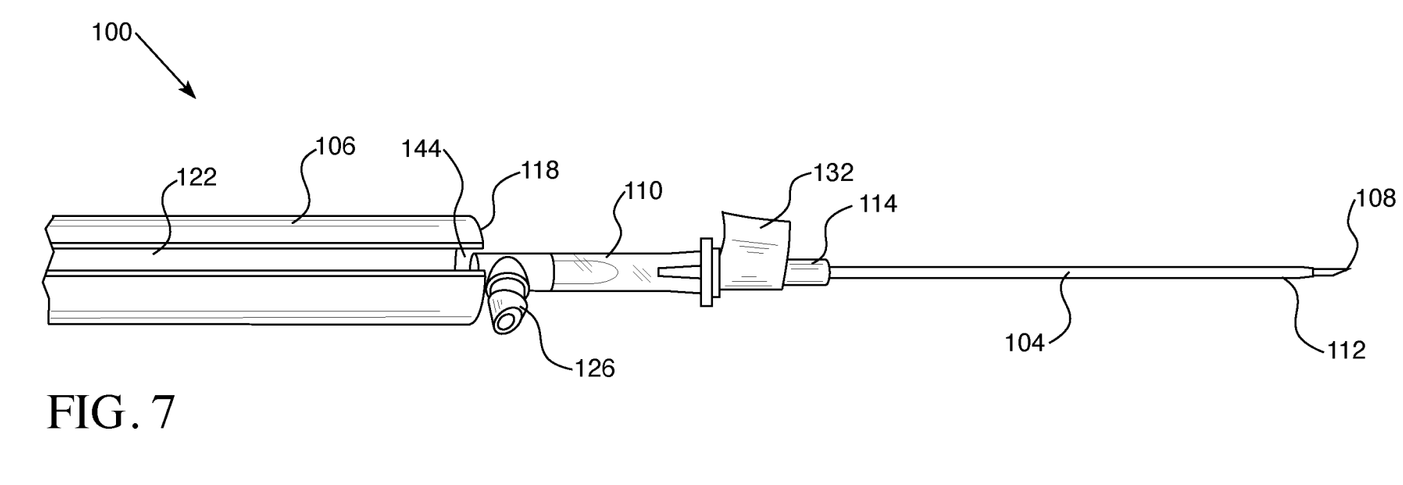
FIG. 7 is a side view of the needle decompression assembly with the needle and catheter fully deployed from the housing, in accordance with one embodiment of the invention.

For example, as shown in FIG. 4, the needle 102 and catheter 104 are deployed only to the first length setting for the shortest deployed needle length in order to treat a small patient. If the medical provider determines that the patient is medium sized, then the needle 102 and catheter 104 are deployed to the second length setting, shown in FIG. 5, so the exposed needle length is greater than the exposed needle length in the first length setting. One of ordinary skill in the art would readily understand that the housing 106 may include several length settings along the length of the housing 106, including more or fewer length settings than are depicted herein. For the largest patients that have a thicker chest wall, the needle 102 and catheter 104 may be entirely deployed out of the distal end 118 of the housing 106, rather than being only partially deployed in accordance with the different length settings. FIG. 7 depicts the needle 102 and catheter 104 being completely deployed out of the distal end 118 of the housing 106.

The needle length adjustment mechanism may be any mechanism that allows the user to quickly and easily selectively deploy a desired length of the needle 102 and the catheter 104 out of the distal end 118 of the housing 106. When the housing cap is removed, the distal ends of the needle 102 and the catheter 104 extend from the distal end 118 of the housing 106. In one embodiment, as shown in FIGS. 1 and 3-7, the length adjustment mechanism comprises an axial path 122 along the length of the housing 106, a plurality of grooves 124 extending perpendicularly off of the axial path 122, a protruding arm 126 coupled to the needle 102, and a protruding tab 132 coupled to the catheter 104. The axial path 122 and the grooves 124 are passages that extend through the thickness of a wall of the housing 106. The protruding arm 126 and protruding tab 132 are configured to extend out of the housing 106 through the axial path 122 and/or the grooves 124. The outer surface of the housing 106 may include markings to guide the user to the appropriate exposed needle length. For example, in the present embodiment, each one of the grooves 124 may be marked with a label in order to assist the user in selecting an appropriate needle length. The groove 124 closest to the proximal end 116 of the housing 106 is for holding the needle 102 and catheter 104 in place during storage and transportation. The remaining grooves 124 are for locking the needle 102 and catheter 104 in a desired axial position. Depth markings along the length of the housing assist the user in determining how far the needle distal end 108 should extend from the housing open end 118. The axial path 122 comprises a closed proximal end 142 and an open distal end 144. The open distal end 144 of the axial path 122 allows the needle 102 and catheter 104 to be completely removed from the housing 106 by moving the protruding arm 126 distally relative to the housing 106 until the protruding arm 126 exits out of the open distal end 144 of the path 122, as shown in FIG. 7.

The protruding arm 126 is coupled to, and extends perpendicularly to, the needle hub 110 at the proximal end of the needle 102. The protruding arm 126 is fixedly attached to the needle 102 via the needle hub 110 so that the protruding arm 126 cannot be removed from the needle 102. The protruding arm 126 is sized and shaped to fit within the axial path 122 and the grooves 124. The protruding arm 126 is also sized and shaped to be grasped and maneuvered by a user. That is, a user may grasp the protruding arm 126 and guide it distally or proximally along the axial path 122 until the arm 126 is aligned with one of the grooves 124. When the needle 102 is being moved axially relative to the housing 106, the protruding arm 126 is disposed within the axial path 122. When the needle 102 is deployed to a desired length, the needle 102 and the protruding arm 126 are rotated relative to the housing 106 so that the protruding arm 126 is disposed in one of the grooves 124, thus locking the needle 102 in place relative to the housing 106. The protruding arm 126 is made of a material that is sufficiently rigid so that the needle 102 is held in place by locking the protruding arm 126 into position in one of the grooves 124. The protruding arm 126 may fit within the groove 124 with a friction fit. After locking the needle 102 into place with the protruding arm 126 disposed in one of the grooves 124 and the distal end 108 of the needle 102 deployed to a desired length, then the kit 100 can be used to perform needle decompression on the patient.

The needle 102 is disposed within the catheter 104. The needle 102 and catheter 104 may be coupled together so that the needle 102 and catheter 104 may not be moved axially relative to each other. For example, the needle 102 may have an outer diameter that is similar to, or slightly smaller than, the inner diameter of the catheter 104 so that the needle 102 is held within the catheter 104 in a friction fit. The needle 102 and catheter 104 may be configured to rotate relative to each other when the needle 102 is disposed in the catheter 104. Alternatively, the needle 102 and catheter 104 may be locked together to prevent axial and rotational movement between the needle 102 and the catheter 104 and the tab 132 attached to the catheter 104 may be sufficiently flexible. After the needle 102 and catheter 104 are positioned in the pleural space of the patient, the needle 102 may be dislodged, or unlocked, from the catheter 104 so that the needle 102 can be removed from the patient's chest while the catheter 104 remains in place. Alternatively or additionally, after the needle 102 and the catheter 104 are correctly positioned in the pleural space, the needle 102 may be withdrawn while the catheter 104 is advanced slightly further into the pleural space.

Figure 6:
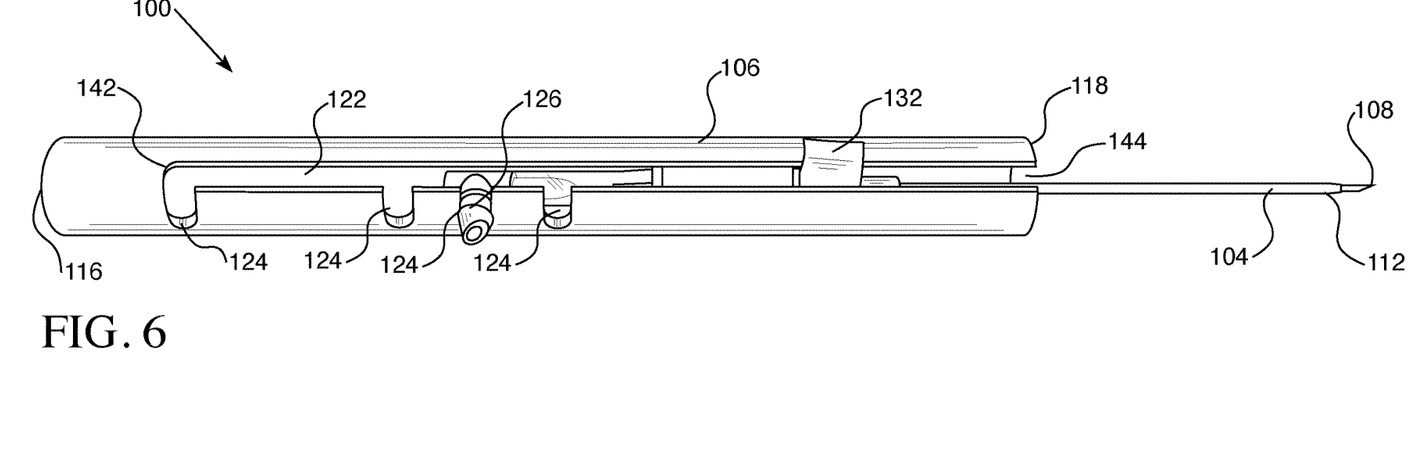
FIG. 6 is a side view of the needle decompression assembly during catheter deployment, in accordance with one embodiment of the invention.

The protruding tab 132 attached to the catheter hub 114 extends perpendicularly relative to the longitudinal axis of the catheter 104. When the catheter 104 is disposed inside of the housing 106, the tab 132 protrudes through the axial path 122. The tab 132 is sized and shaped to be grasped by a user. For example, as shown in FIG. 6, the catheter 104 is held in place during removal of the needle 102 and the housing 106 by a user grasping the tab 132 to hold the catheter 104 in place while the needle 102 and housing 106 are removed proximally relative to the catheter 104. In addition, the user may use the tab 132 to advance the catheter 104 slightly further into the pleural during or after removal of the needle 102 and housing 106. The protruding tab 132 may be made of a material that is sufficiently long and flexible so that when the needle 102 and catheter 104 are rotated in order to lock the protruding arm 126 into one of the grooves 124, the protruding tab 132 includes an outer portion that extends out of the axial path 122 and includes an inner portion that rotates with the catheter 104. Alternatively, the protruding tab 132 may be made of a rigid material that protrudes through the axial path 122. In this embodiment, the needle 102 is configured to rotate relative to the catheter 104 so that the rigid protruding tab 132 can remain in place when the needle 102 is rotated to position the protruding arm 126 in one of the grooves 124. The protruding tab 132 may be fixedly attached to the catheter 104 or may be removed after the catheter distal end 112 is positioned in the patient's pleural space and the needle 102 and housing 106 are withdrawn.

It will be well understood by a person of ordinary skill in the art that another needle length adjustment mechanism could be used. For example, the mechanism to adjust the length of the exposed needle could be similar to the mechanism used to deploy pencil lead in a mechanical pencil, where the proximal end of the device is pressed repeatedly until the desired length of needle extends from the distal end of the housing. The needle length adjustment mechanism can be any mechanism that is reliable, quick, and easy to use by a medical provider in an emergency, pre-hospital setting, such as a battlefield or the like.

Figure 8:
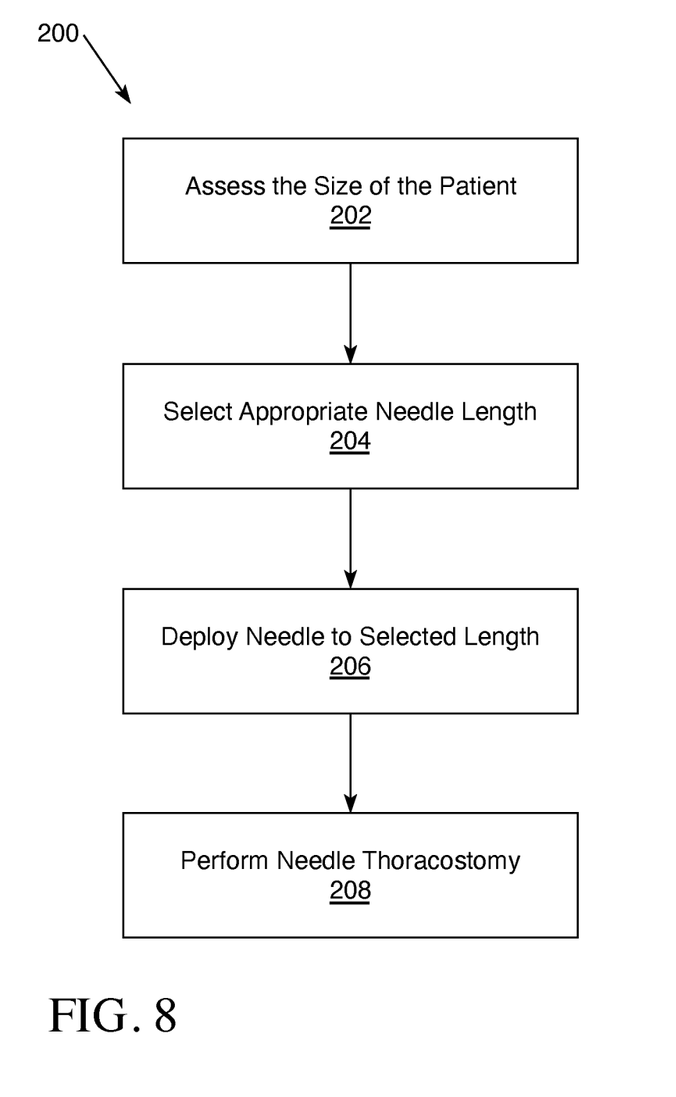
FIG. 8 is a flow chart of a method for treating tension pneumothorax using the needle decompression assembly, in accordance with one embodiment of the invention.

A method 200 of using the needle decompression kit 100 is shown in FIG. 8. In a first step 202 of the method 200, the medical provider assesses the size of the patient to determine an approximate thickness of the chest wall. Next, in step 204, the medical provider selects an appropriate exposed needle length based on the size of the patient. Next, in step 206, the medical provider removes the cap from the housing 106 and deploys the catheter 104 with the needle 102 disposed therein to the desired length out of the distal end 118 of the housing 106. The catheter 104 and needle 102 may be deployed by grasping the protruding arm 126 that extends off of the needle 102, moving the protruding arm 126 along the axial path 122 in the housing 106 until the desired length of the catheter 104 and needle 102 are exposed out of the distal end 118 of the housing 106. Once the desired length of the needle 102 and catheter 104 are deployed out of the distal end 118 of the housing 106, the needle 102 and catheter 104 may be locked into place by rotating the needle 102 and moving the protruding arm 126 from the axial path 122 into the groove 124 that corresponds with the desired needle length. Finally, after the needle 102 and catheter 104 are deployed to the appropriate length for the size of the patient, a needle thoracostomy is performed in step 208, wherein the needle 102 and catheter 104 are used to puncture the skin, pass through the chest wall, and position the catheter distal end 112 in the patient's chest cavity in order to treat tension pneumothorax. The needle 102 and the housing 106 are withdrawn after the catheter distal end 112 is positioned in the pleural space.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for performing needle decompression using an adjustable length needle through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. A needle assembly comprising:
   an elongated needle having a sharp distal end and a proximal end coupled to a needle hub;
   an elongated catheter having a distal end, a proximal end coupled to a catheter hub, and a lumen extending from the distal end to the proximal end, wherein the needle is sized and shaped to fit in the catheter lumen so that the needle distal end protrudes from the catheter distal end and the needle hub at the needle proximal end engages with the catheter hub at the catheter proximal end; and
   a housing comprising a closed proximal end, an open distal end, and a housing lumen extending from the closed proximal end to the open distal end,
      wherein the housing lumen is sized and shaped so that the needle disposed in the catheter lumen is entirely contained within the housing, and
      wherein the needle is coupled to the housing through a length adjustment mechanism so that the needle and the catheter are configured to be deployed out of the distal end of the housing to a pre-determined length.

2. The assembly of claim 1, wherein the housing further comprises demarcations that are visible to a user in order to assist the user in selecting the pre-determined length to be deployed from the housing.

3. The assembly of claim 1, wherein the length adjustment mechanism comprises an axial path in a wall of the housing and grooves extending perpendicularly from the axial path.

4. The assembly of claim 3, further comprising a protruding arm extending from the needle hub and a catheter tab extending from the catheter hub, wherein the protruding arm and the catheter tab are sized and shaped to protrude out of the axial path and the grooves in the housing and to be grasped and manipulated by a user when the needle and catheter are disposed inside the housing.

5. The assembly of claim 4, wherein the catheter tab is made of a flexible material so that an inner portion of the tab is configured to rotate with the catheter while an outer portion of the tab protrudes out of the axial path in the housing.

6. The assembly of claim 3, wherein the axial path comprises a proximal end disposed distally of the housing proximal end, and wherein the axial path comprises a distal end in communication with the housing distal end.

* * * * *

UNITED STATES PATENT AND TRADEMARK OFFICE
CERTIFICATE OF CORRECTION

Page 1 of 1

PATENT NO. : 12,090,289 B2
APPLICATION NO. : 17/474706
DATED : September 14, 2021
INVENTOR(S) : John M. Couzens and David A. Lux It is certified that error appears in the above-identified patent and that said Letters Patent is hereby corrected as shown below:

On the Title Page

Item (71) Applicant, delete "CZDX Solutions, LLC, Southern Pines, NC (US)", and insert therefor --Safedart C.L LLC, Southern Pines, NC (US)--; and Item (73) Assignee, delete "CZDX Solutions, LLC, Southern Pines, NC (US)", and insert therefor --Safedart C.L LLC, Southern Pines, NC (US)--.

Signed and Sealed this
Seventeenth Day of June, 2025

Coke Morgan Stewart
*Acting Director of the United States Patent and Trademark Office*